United States Patent [19]

Ruell

[11] 4,336,998
[45] Jun. 29, 1982

[54] FINGERPRINT TRANSDUCER AND READING APPARATUS

[75] Inventor: Hartwig Ruell, Mt. Laurel, N.J.

[73] Assignee: Siemens Corporation, Iselin, N.J.

[21] Appl. No.: 152,514

[22] Filed: May 22, 1980

[51] Int. Cl.³ .......................... G06K 7/10; G06K 9/00
[52] U.S. Cl. ............................. 356/71; 340/146.3 E; 365/126
[58] Field of Search ................. 340/146.3 E; 356/71; 264/75, 40.1, 340, 230; 346/1, 21, 77 E; 365/106, 127, 126; 350/286, 287

[56] References Cited

U.S. PATENT DOCUMENTS

| | | | |
|---|---|---|---|
| 2,777,987 | 1/1957 | Walkup | 430/902 |
| 2,856,533 | 10/1958 | Rosenthal | 430/902 |
| 2,922,883 | 1/1960 | Giamo | 430/902 |
| 3,542,545 | 11/1970 | Goffe | 365/126 |
| 3,764,311 | 10/1973 | Bean | 365/126 |
| 3,858,973 | 1/1975 | Heurtley | 365/126 |
| 3,871,002 | 3/1975 | Shädlich et al. | 365/126 |
| 4,015,248 | 3/1977 | Pekau et al. | 365/126 |
| 4,065,308 | 12/1977 | Bergen | 365/126 |

Primary Examiner—Willard E. Hoag
Attorney, Agent, or Firm—Spellman, Joel & Pelton

[57] ABSTRACT

The fingerprint transducer contains a sensing member having a sensing surface for receiving a fingerprint, a device for generating an electrostatic charge on the sensing surface and a heating device for heating the sensing surface up to a temperature which is approximately the softening temperature of the sensing member. The method for enhancing fingerprints comprises the steps of generating the fingerprint on the sensing surface, electrostatically charging the sensing surface, heating the sensing surface up to the softening temperature, and thereafter cooling down the sensing member.

14 Claims, 1 Drawing Figure

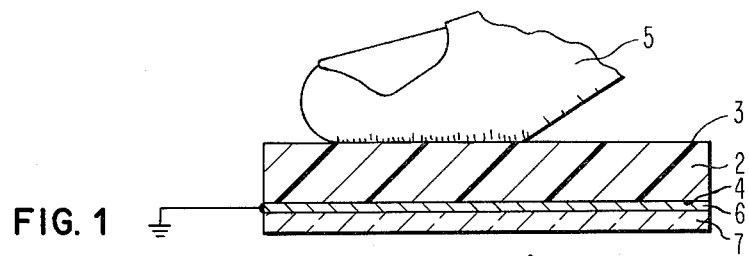
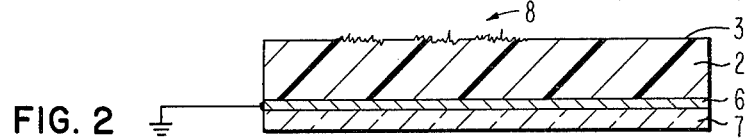
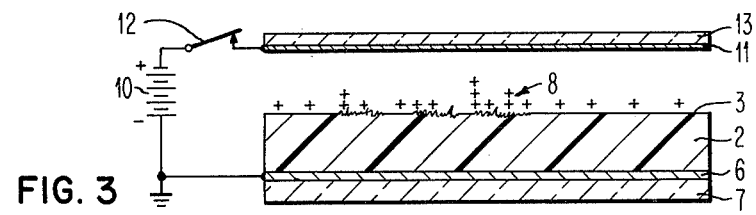
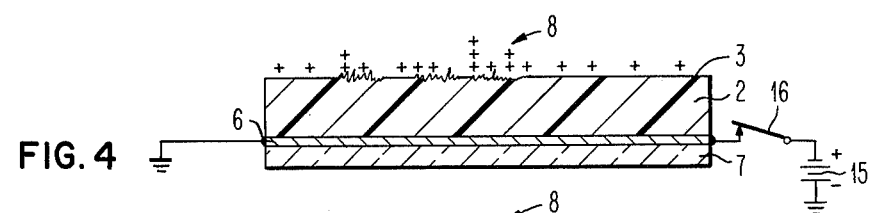
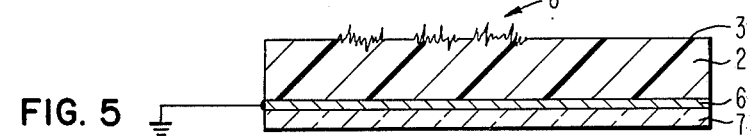
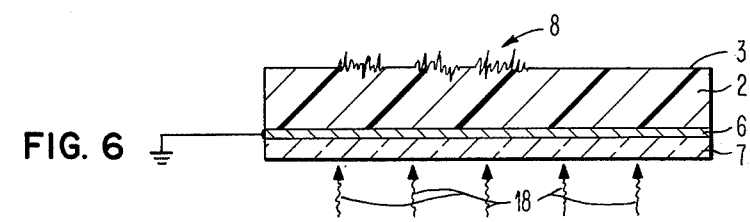
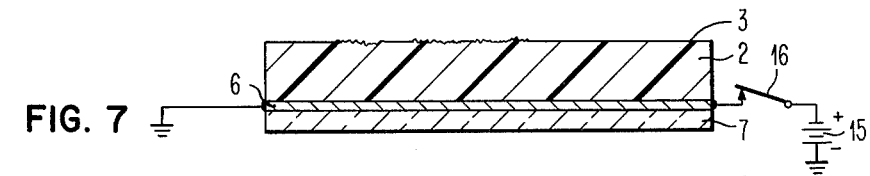
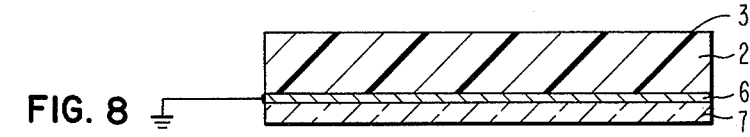

FINGERPRINT TRANSDUCER AND READING APPARATUS

FIELD OF THE INVENTION

This invention relates to an apparatus for identification of fingerprints. In particular, this invention relates to an input transducer or input sensor for sensing a fingerprint and entering corresponding information into a fingerprint identification device. Still more particularly, this invention relates to a transducer having a surface for pressing a finger thereto. The invention also relates to a method for enhancing and storing fingerprints even of poor quality.

CROSS-REFERENCE TO RELATED APPLICATION

This application relates to the same technical field as the commonly-owned, copending U.S. patent application Ser. No. 152,513, of H. Ruell, et al., entitled "Transducer for Fingerprints and Method for Analyzing Fingerprints", filed May 22, 1980.

BACKGROUND OF THE INVENTION

In a fingerprint input transducer or sensor, the finger under investigation is usually pressed against a flat surface, such as one side of a glass plate, and the ridge-valley pattern of the finger is sensed by some sensing means such as an interrogating light beam. The processing of the fingerprint information thus obtained may comprise laser techniques. Such fingerprint identification devices are generally used to control the access of individuals to information, for instance computer terminals (information access control) or buildings (physical access control).

One of the problems associated with fingerprint sensors concerns the reliable sensing of weak fingerprints. "Weak fingerprints" are fingerprints which have a small modulation depth on the sensing surface, or in other words, a small amount of topographic relief. A weak fingerprint may occur when the finger under test is not firmly pressed against the surface, when the finger does not have sufficient fluid such as oil or moisture to leave sufficient traces on the surface, etc.

Therefore, there is a need for a fingerprint input sensor or transducer which is adapted to sense not only fingerprints of regular quality, but also weak fingerprints of small modulation depth. There is also a need for a method for enhancing fingerprints.

The U.S. Pat. No. 4,053,228 discloses a finger identification system in which a fingerpress is formed by pressing a finger against the back surface of a transparent glass plate and holding it in a predetermined position thereon. This fingerpress is interrogated by a light beam directed through the front surface of the glass plate. The interrogating beam is partially reflected at the back surface of the glass surface to provide a signal beam, carrying fingerpress information. The back surface of the glass plate is coated with a coating to enhance the difference in reflectivity of the valleys and crests of the fingerpress. In particular, the coating on the back surface enhances the difference in reflection at that surface between those areas where the crests of the finger are in intimate contact with the back surface of the plate and those areas under the valleys of the finger, where air is in contact with the back surface of the plate. In this fingerprint transducer an enhanced fingerpress will only be created as long as the finger engages the back surface of the plate, that is for a short while.

U.S. Pat. No. 4,120,585 discloses a pliable, resilient prism for use in an optical imaging system such as a fingerprint reader. The base surface of the prism is contacted by the finger under investigation. The pliable prism deforms under the pressure of the contacting finger. Light from a light source passes through one side face of the prism to the base surface from where it is reflected and passed through the other side face to a photosensitive element. This element is provided for actuating the optical imaging system. If there is sufficient finger pressure, an air gap will be created between the base surface and a housing, resulting in an additional area the light beam of which is directed to the photosensitive element. This element will activate the system by closing of a switch. In this fingerprint system, no means are discussed to process weak fingerprints.

In SPIE, Vol. 185, Optical Processing Systems (1979), pp. 86–92, an elastomer storage device is disclosed which uses a photoconductor. A glass substrate is chemically etched to form a transparent conductive ground plane. The ground plane is coated with the mentioned photoconductor and overcoated with a thin elastomer layer. A charge plane is positioned several mils above, and parallel to, the elastomer surface. The resulting gap is filled with low pressure argon. In operation, a high voltage source is connected between the charge plane and the ground plane, producing an electrostatic force across the elastomer and photoconductor layers. The electrostatic force is normal to the elastomer surface and is proportional to the electric field strength at each point. Because the elastomer is incompressible and the force is uniform, no deformation occurs. When the photoconductor is exposed to a light distribution, charge carriers are photogenerated and move in the electric field to the elastomer-photoconductor interface where they are trapped. The trapped charges form an electrostatic surface charge layer in which the charge density distribution is directly proportional to the exposure distribution of the input signal. The resulting electric field distribution causes the elastomer to deform creating a surface relief pattern which is directly related to the exposure distribution through the surface charge density. The deformation will continue as long as the non-uniform charge distribution is maintained. This storage device, incidentally, is not contemplated for use as a fingerprint transducer.

In SPIE, Vol. 123, Optical Storage Materials and Methods (1977), pp. 32–36, a thermoplastic data storage medium is disclosed. This medium is a multilayered device consisting of a thermoplastic layer, a photoconductor layer, and a transparent conductive layer coated on a glass or flexible polyester substrate. The optical data storage in thermoplastic is based on the principle that thermoplastic deforms under stress when heated to an appropriate temperature. During writing, a uniform charge is applied to the thermoplastic surface. The device is then exposed to a holographic pattern which alters the conductivity of the photoconductor and thus the surface charge distribution. This non-uniform charge distribution results in electrostatic forces which deform the thermoplastic upon heating to a critical softening/developing temperature. When the sample cools, the deformation corresponding to the holographic pattern remains and the information can be retrieved by illumination with a reference beam. Also this storage medium is not contemplated for use as a fingerprint transducer.

Similar optical recording and storage devices are known from SPIE, Vol 123, Optical Storage Materials and Methods (1977), pp. 10–16, and pp. 74–77.

BRIEF DESCRIPTION OF THE INVENTION

Objects

It is an object of the present invention to provide a fingerprint input sensor or transducer which is capable of detecting and sensing even weak fingerprints that have only a small modulation depth.

It is another object of this invention to provide a fingerprint transducer which enhances the relief of a fingerprint that is applied to a surface.

It is another object of this invention to provide a fingerprint transducer wherein a fingerprint can be stored for a short period of time.

It is still another object of this invention to provide a method or process for enhancing a fingerprint which is applied to a surface.

Summary

According to this invention, the fingerprint input transducer contains a sensing member having a sensing surface for receiving a fingerprint, a device for generating an electrostatic charge on the sensing surface, and a heating device for heating the sensing surface of the sensing member up to a temperature which is approximately the softening temperature of the material of which the sensing member is made. The softening temperature must be higher than the ambient temperature of the fingerprint input transducer. Generally, the softening temperature of the sensing member should be above 40° centigrade.

The sensing member may be made of an elastic or resilient material. Preferably it is made of an elastomer or a thermoplastic material, for instance a plasticized polystyrene. It may also be made of a material the properties of which are similar to those of an elastomer. An elastomer is any of those various polymers having the elastic properties of natural rubber. In particular, an elastomer of a comparatively low softening temperature may be chosen.

In another preferred embodiment of the fingerprint input transducer, the softening temperature is chosen to be only a few degrees centigrade above the temperature of the human body.

In operation of the input transducer, in a first step, the finger under investigation is pressed against the surface of the sensing member so that it leaves behind a surface relief. Dependent on the pressure of the finger and the amount of oil or moisture left behind, the modulation depth of the fingerprint is more or less sufficient for ordinary sensing of the surface. The surface of the sensing member is then charged electrostatically by the charging device. Due to the relief of the surface, the distribution of the charges will not be homogeneous. The distribution of the charges represents an exact image of the structure of the relief. Subsequently, the sensing member, at least its sensing surface, is heated to a temperature which is near to the softening temperature, whereby the sensing member becomes soft on its sensing surface. The material of the softened sensing member will follow the electric force (exercised by the electric field) which is different from surface element to surface element in accordance with the locally varying charge density. In other words, the surface will be raised in certain surface elements and depressed in others. This raising and lowering of the surface has the tendency to enhance the relief on the surface and to increase the degree of modulation. In other words, the valleys of the fingerprint pattern on the surface will become deeper, and the ridges will become higher. Thus, the rippled surface on the sensing member will obtain a more distinct topographic relief. Subsequently the sensing surface is cooled down so as to "freeze in" the enhanced relief.

The charge may be preferably applied to the surface by corona charging. For this purpose, the charging device may contain a wire which is arranged at some distance from the surface of the sensing member, and a voltage source for supplying a DC voltage between the wire and the surface of the sensing member. The charging device may also comprise an areal electrode in the shape of a wire-lattice which is located close to the surface of the sensing member, and a voltage source for applying a DC voltage between the electrode and the sensing member.

The heating device may be an electric heating device. It may contain a heating resistor, which is, for instance, a resistance wire, an areal wire-lattice or a transparent electrode having some appropriate area-resistance. When activated, a heating current will flow through the heating resistor. The wire-lattice may be transparent with regard to the wavelength of a sensing light beam. In order to achieve good heat coupling, the heating resistor may be attached to the sensing member.

However, the heating device does not need to be an ohmic or resistive heating device. Heating can also be performed by radiation. For instance, heat can be transferred to the sensing surface by means of an infra-red (IR) laser, particularly an IR LED, by means of a semiconductor laser or by similar IR light sources.

The fingerprint information stored in the sensing member may be read out either by optical means such as by total reflection or by laser optics, in a well-known manner. The topographic relief can be analyzed in any manner which is known in the art.

One of the advantages of the present invention is that the enhanced relief on the surface of the sensing member will remain stable or "frozen in" after the heating device has been switched off and the sensing member has cooled down.

In order to extinguish the relief, the sensing surface is heated again without electrostatically charging the surface. For instance, heating current may again be sent through the heating resistor which is coupled thermically to the elastomer. By heating the sensing surface again, the surface will become soft, and the melting surface will be flattened due to surface tension. The transducer will thus be prepared for a new fingerprint identification cycle. For extinguishing the relief, the heating temperature should be higher than for the preceding enhancement of the surface relief.

A method for enhancing a fingerprint according to the invention thus comprises the steps of generating the fingerprint on the sensing surface of a sensing member, electrostatically charging the sensing surface, heating the sensing surface up to a temperature which is approximately the softening temperature of the material of the sensing member, and cooling down the sensing member to a temperature which is below the softening temperature.

The foregoing and other objects, features and advantages of the invention will be apparent from the following more particular description of the preferred embodiments of the invention, as illustrated in the accompanying drawings.

BRIEF DESCRIPTION OF THE DRAWINGS

In the drawings:

FIGS. 1-8 show an embodiment of the fingerprint transducer and illustrate a method of operation of the transducer;

DETAILED DESCRIPTION OF THE PREFERRED EMBODIMENTS

Figure 9:
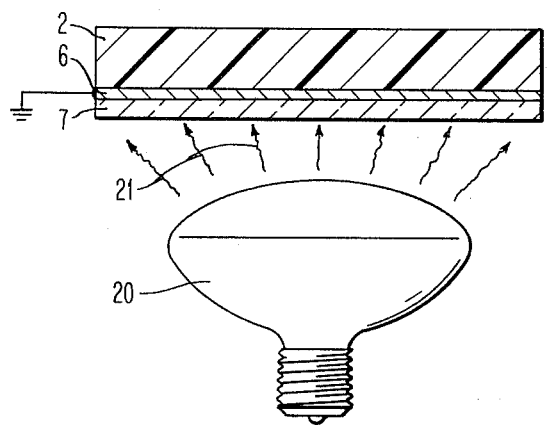
FIG. 9 shows a fingerprint transducer according to the invention which can be heated by an IR light source.

According to FIG. 1, a rectangular flat plate is provided as a sensing member 2. The sensing member 2 has a first or sensing surface 3 and a second surface 4. The sensing member 2 is made of an elastic material, which is reusable, preferably of an elastomer or a thermoplastic material such as plasticized polystyrene. The material of the sensing member 2 is electrically non-conductive. It is chosen such that its softening temperature is higher than the ambient temperature surrounding the member 2. Particularly, the softening temperature should be chosen to be more than about 40° centigrade. It may be chosen to be only a few degrees centigrade above ambient temperature. The sensing surface 3 is designed to receive, for a short period of time, the pressure of a finger 5 under investigation. Departing from the illustration of FIG. 1, the sensing surface 3 of the sensing member 2 does not need to be flat. It may also be curved in such a way as to match the outline of the finger 5.

Attached to the second surface 4 is an electrode 6. The electrode 6 is preferably made of a material which is transparent with regard to the light of an interrogating beam (see FIG. 6). It may be made of indium oxide (InO). The electrode 6 is in the form of a thin rectangular plate or wire system or may be a thin film coating. The electrode 6 may be connected to ground. It is supported by a light transparent supporting plate 7, for instance a glass substrate.

In a first operational step, the finger 5 is pressed against the flat sensing surface 3 of the sensing member 2. This can be seen in FIG. 1.

As is illustrated in FIG. 2, the second operational step is to remove the finger 5 from the sensing surface 3. A fingerprint 8 is left behind on the surface 3. Due to a small pressure or a worn fingerprint structure, the fingerprint may only be weak. In the course of the following operational steps, even a weak fingerprint 8 will be enhanced sufficiently so that processing of the fingerprint information is possible.

It should be pointed out that the sensing surface 3 can be impressed by the finger 5. When the finger 5 rests on the surface 3 the surface 3 will receive a non-even surface structure. Due to the pressure and the heat of the finger 5, the surface 3 will adjust to the surface structure of the finger 5. This is similar to the process of coining. It is sufficient for the purpose of the present embodiment if the sensing member represents a "short-time fingerprint memory" and will retain its original status, that is an even surface 3, after some time.

As illustrated in FIG. 3, the third step in the operation of the fingerprint sensor comprises electrostatic charging. For this purpose, an electrostatical charging device is provided. This device contains a voltage source 10 havng a high voltage V which can be connected electrically between ground and an electrode 11 by means of a switch 12. The electrode 11 is arranged in some distance from the sensing surface 3. It is carried by a carrying member 13, for instance a glass substrate. The electrode 11 may be a single wire which is arranged parallel to the surface 3. In the present embodiment it is a plane electrode which is connected to the lower surface of the carrying member 13.

As soon as the switch 12 is closed, the high voltage V between the electrodes 6 and 11 will cause ionization of the air close to the electrode 11. Due to the ionization of the air, electrical charges will be directed to the sensing surface 3. These charges are retained on the surface 3. They cannot flow away from the surface 3, since the sensing member 2 is an electrical insulator.

As also illustrated in FIG. 3, the positive terminal of the high voltage source 10 is connected to the electrode 11, whereas the negative terminal is connected to the electrode 4. Therefore, the surface 3 is charged with positive particles. However, charging with negative particles is also possible. To obtain negative electrostatic charging, it is necessary only to reverse the polarity of the high voltage source 10 with regard to the electrodes 4 and 11. As indicated in FIG. 3, the positive particles will preferably gather at certain surface elements in the region of the fingerprint 8. Due to the locally varying charge density, different electrical field strengths are present, and different electric forces will be exercised on different surface elements.

Illustrated in FIG. 4 is the fourth step in the operation of the fingerprint sensor. This fourth step is heating of the surface 3. It can be compared to a "developing process" concerning the fingerprint. Heating is achieved by a heating device which in the present embodiment is of electrical nature, particularly as a resistive heating device. The heating device contains a heating current source 15 and a switch 16. The heating current source 15 and the switch 16 are connected in series between the one end of the electrode 6 and ground. The other end of the electrode 6 is also connected to ground. Note that the charging device 10-13 is switched off. By closing the switch 16, the heating current source 15 will emit a heating current (d-c or pulsed) that flows through the electrode 6. Thus, the electrode 6 is not only a high-voltage electrode used for electrostatically charging. It is simultaneously a heating resistor, for instance a resistance grid. The heating current will heat the sensing member 2. The value of the heating current is such as to achieve a temperature on the sensing surface 3 which is at least approximately the softening temperature of the elastomer or the thermoplastic material. In the course of the heating process the surface 3 of the sensing member 2 will become soft and almost start to melt. Due to the electrical force which vary locally across the fingerprint 8, the ridges are elevated towards the electrode 11. Thus, the topographic relief of the fingerprint 8 on the surface 3 is enhanced. The enhancement corresponds to the local distribution of the electric field on the surface 3.

In FIG. 5 is illustrated the enhanced pattern of the fingerprint 8.

According to FIG. 5, the fifth operational step is cooling down the sensing member 2. This can be achieved simply by switching off the switch 16, provided that the ambient temperature is low enough. In addition, some cooling device (not shown) such as thermoelectric Peltier elements may be connected to the sensing member 2. Cooling down of the sensing member 2 results in a "freezing in" of the enhanced relief of the surface 8. It should be noted that during the cooling down operation the electrode 11 is switched off from the high voltage source 10.

In FIG. 6 is shown the sixth operational step. In this step, the information contained in the (freezed) fingerprint 8 is read out and analyzed. This can be performed by light of an interrogating or reading beam 18. This beam 18 may be directed to the lower surface 4 of the sensing member 2. The light 18 is transmitted through the transparent member 7 and the transparent electrode 6 into the sensing member 2. Finally it arrives at the upper surface 3. After having passed the fingerprint 8 it carries the fingerprint information. In accordance with the valleys and ridges of the surface 3, the light is spatially modulated, that means it carries the information about the geometrical structure of the fingerprint 8. Analyzing of the information contained in the modulated light may be performed in any way known in the art.

FIG. 7 shows the seventh operational step. In this step, the sensing member 2 is heated again. Heating is also achieved in this case by closing the switch 16. Since the electrode 11 does not send positive particles towards the surface 3 any more, electric particles cannot pile up on the ridges of the fingerprint 8. As soon as the softening temperature of the sensing member 2 is achieved or exceeded, the surface 3 becomes flat again. In other words, the information contained in the fingerprint 8 is extinguished, that is the surface relief is erased.

FIG. 8 shows the eighth and last step of the operation. In this step, the sensing member 2 is cooled down again by opening the switch 16. This time the flat surface 3 is "frozen in". The sensing member 2 is now ready for the next fingerprint processing and reading cycle.

FIG. 9 illustrates that the heating of the sensing member 2 (see FIGS. 4 and 7) can also be obtained by a radiation heating device. In this case, an IR radiation source 20 is used which emits IR radiation 21 towards the lower side of the electrode 6. The IR source 20 may be a single IR source or an array or single IR sources. As IR source 20, an IR emitting LED or an IR bulb may be used.

Figure 10:
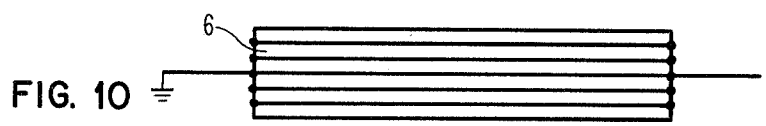
FIG. 10 shows a top view of an electrode which can be used in a transducer according to the invention.

In FIG. 10 is illustrated an embodiment of the electrode 6. The electrode 6 may be an array of parallel resistance wires. These wires may serve as well as electrode in the electrostatic charging process as a heater in the heating process.

Figure 11:
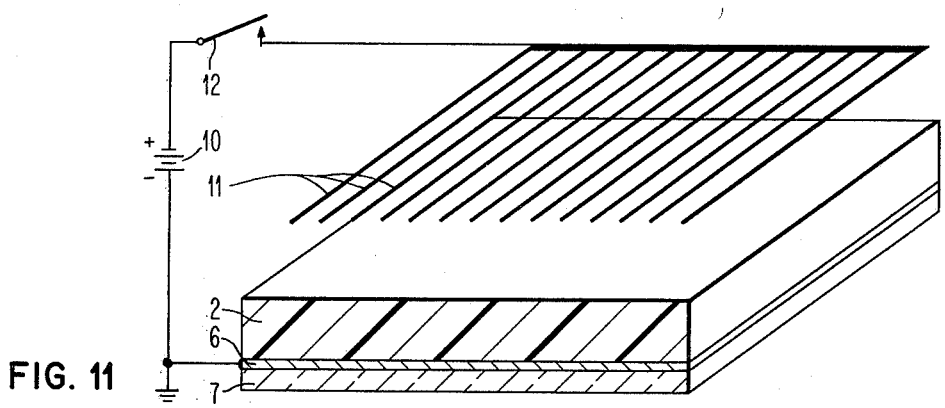
FIG. 11 shows a perspective view of an embodiment of the invention having a grid-type charging electrode.

In FIG. 11 is illustrated a perspective view of another embodiment of the invention. In this embodiment, the electrode 11 for charging the upper surface of the member consists of an array of parallel wires which are connected on one side to a connector 23 which in turn is connected via the switch 12 to the high-voltage source 10. The array of parallel wires may be retained by some suitable device (not shown).

Figure 12:
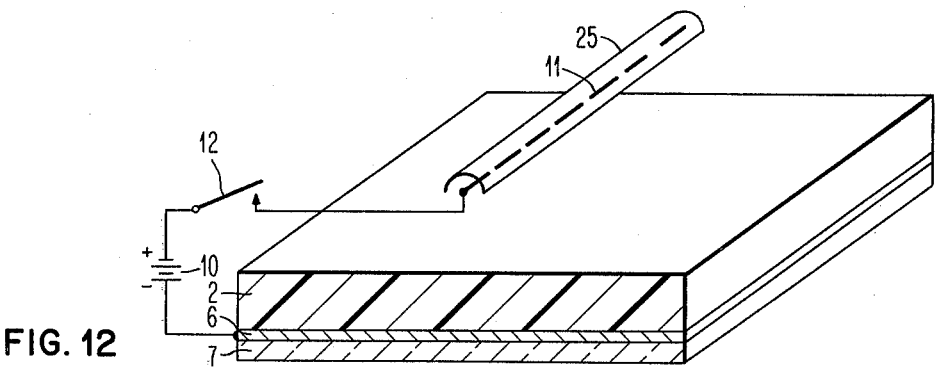
FIG. 12 shows a perspective view of another embodiment of the invention having a single wire as charging electrode.

In FIG. 12 is shown a perspective view of still another embodiment of the invention. In this embodiment, the electrode 11 is a single wire which is retained in parallel to the surface of the member 2. The electrode 11 is screened away from the surface by a screen 25. Therefore, charged particles are generated substantially between the screen 25 and the upper surface of the sensing member 2.

While the form of the fingerprint transducer and the method for enhancing fingerprints herein described constitute preferred embodiments of the invention, it is to be understood that the invention is not limited to these precise forms of assembly and steps, and that a variety of changes may be made therein without departing from the scope of the invention.

What is claimed is:

1. In an apparatus for the identification of fingerprints having a fingerprint sensing member with a sensing surface and having means for interrogating with a light beam a fingerprint relief impressed onto the sensing surface, whereby the light beam is modulated in accordance with the structure of the fingerprint, the improvement comprising:

the sensing surface being made of an insulating material having a softening temperature greater than ambient temperature and which will deform when a finger is pressed thereon to form the fingerprint relief;

means for imparting a non-uniform electrostatic charge distribution to the sensing surface in accordance with the fingerprint relief; and means for heating the sensing surface so that the material softens and produces an enhanced fingerprint relief in response to the electrostatic forces exerted by the electrostatic charge.

2. The improvement according to claim 1, wherein said sensing member is a flat plate.

3. The improvement according to claim 1, wherein said means for heating comprises a heating resistor which is thermically conductively connected to said sensing member and a heating current source for transmitting a heating current through said heating resistor.

4. The improvement according to claim 1, wherein said means for heating comprises an infra-red radiation source which is arranged in some distance from said sensing member.

5. The improvement according to claim 1, wherein the material of said sensing member is a thermoplastic material.

6. The improvement according to claim 1, wherein the material of said sensing member is an elastomer.

7. The improvement according to claim 6, wherein said elastomer is a plasticized polystyrene.

8. The improvement according to claim 1, wherein said means for generating an electrostatic charge comprises a first electrode arranged in some distance in front of said sensing surface and a voltage source for generating a high voltage between said first electrode and said sensing surface.

9. The improvement according to claim 11, wherein said means for heating comprises a third electrode which is constructed as a heating resistor and is thermically conductively connected to said sensing member, and wherein said means for heating further comprises a heating current source for transmitting a heating current through said third electrode.

10. The improvement according to claim 8, wherein said first electrode is an areal wire-lattice.

11. The improvement according to claim 8, wherein said sensing member has a surface portion to which is attached a second electrode, and wherein said high voltage source is adapted to be electrically connected between said first and second electrode.

12. The improvement according to claim 11, wherein said sensing member is a flat plate having a first and a second side, which are substantially parallel, wherein said first side is said sensing surface, wherein said second side is said surface portion to which is attached said second electrode, wherein said first electrode is a wire which is arranged parallel to said sensing surface, and wherein said second electrode is an areal electrode covering substantially the second side of said plate.

13. The improvement according to claim 12, wherein said second electrode is at least partially transparent for an interrogating beam of light.

14. The improvement according to claim 13, wherein said second electrode is a wire-lattice.

* * * * *